United States Patent [19]

Demers et al.

[11] Patent Number: 4,904,667

[45] Date of Patent: Feb. 27, 1990

[54] 1H-1,2,4-THIADIAZOLO(3,4-B)QUINAZO-LIN-5-ONE-2,2-DIOXIDES, AND A METHOD FOR INCREASING THE CARDIAC OUTPUT OF A MAMMAL WITH THEM

[75] Inventors: James P. Demers, New York, N.Y.; Richard B. Sulsky, Somerville, N.J.

[73] Assignee: Ortho Pharmaceutical Corporation, Raritan, N.J.

[21] Appl. No.: 315,063

[22] Filed: Feb. 24, 1989

[51] Int. Cl.$^4$ .................. A61K 31/505; C07D 513/04
[52] U.S. Cl. .................................... 514/267; 544/250; 558/5
[58] Field of Search .......................... 544/250; 514/267

[56] References Cited

U.S. PATENT DOCUMENTS 4,083,980  4/1978  Schromm et al. .............. 544/250 X
4,548,938 10/1985  Kennis et al. .................... 544/250 X
4,738,964  4/1988  Saeva et al. ......................... 514/267

*Primary Examiner*—Mukund J. Shah
*Assistant Examiner*—Diana G. Rivers
*Attorney, Agent, or Firm*—Charles J. Metz

[57] ABSTRACT

1H-1,2,4-thiadiazolo[3,4-b]quinazolin-5-one-2,2-dioxides are disclosed. These compounds are useful as caridotonic agents. A preferred compound is 7-(n-cyclohexyl-N-methyl-4-amino-4-oxobutyloxy)-1H-1,2,4-thiadiazolo[3,4-b]quinazolin-5-one-2,2-dioxide.

11 Claims, 1 Drawing Sheet

1H-1,2,4-THIADIAZOLO(3,4-B)QUINAZOLIN-5-ONE-2,2-DIOXIDES, AND A METHOD FOR INCREASING THE CARDIAC OUTPUT OF A MAMMAL WITH THEM

The invention relates to novel thiadiazole compounds, to their use as cardiotonic agents, and to a method for producing S-methyl-N-(chloromethanesulfonyl)isothiourea, which is used as an intermediate in the preparation of the novel thiadiazole compounds of the invention.

The thiadiazole compounds of the invention are inhibitors of cyclic nucleotide phosphodiesterase. Inhibition of this enzyme is associated with increased contractility of heart muscle; therefore these compounds can be used as cardiotonic agents. Inhibition of phosphodiesterase is also associated with a decrease in platelet aggregation; therefore, the thiadiazole compounds of the invention may also be useful as antithrombotic agents. The compounds of the invention also show activity in the inhibition of calcium dependent smooth muscle contraction, and therefore may also be useful as broncho dilators.

BRIEF SUMMARY OF THE INVENTION

The novel thiadiazole compounds of the invention are 1H-1,2,4-thiadiazolo[3,4-b]quinazolin-5-one-2,2-dioxides, as represented by Structural Formula I, shown in FIG. 1. The compounds of the invention can be produced by reacting an isatoic anhydride (Structural Formula III) with S-methyl-N-(chloromethanesulfonyl)isothiourea (II), in accordance with the reaction sequence shown in FIG. 2. An improved process for preparing S-methyl-N-(chloromethanesulfonyl)-isothiourea comprises reacting S-methylisothiourea sulfate with chloromethanesulfonyl chloride in the presence of a base such as an alkali metal carbonate, in a two phase reaction mixture comprising water and an organic solvent such as methylene chloride or other organic solvent that is substantially immiscible with water.

THE PRIOR ART

The thiadiazoloquinazolinone ring system has not been previously reported. There exists a 1973 French patent (No. 2,145,005) that discloses fused 1,2,4-thiadiazoline-1,1-dioxides as a general class; this patent also discloses a synthesis of S-methyl-N-(chloromethanesulfonyl)isothiourea by a single-solvent method which applicants herein have been unable to duplicate. The same authors have published a related paper: A. Etienne al., Bull. Chem. Soc. Fr., 7–8, Pt. 2, 1580–1584 (1974).

DETAILED DESCRIPTION OF THE INVENTION

Figure 1:
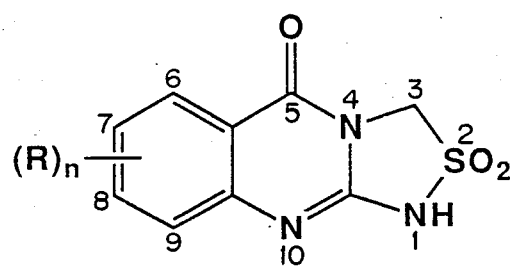
FIG. 1 is a structural formula that represents the novel thiadiazole compounds of the invention.
Figure 2:
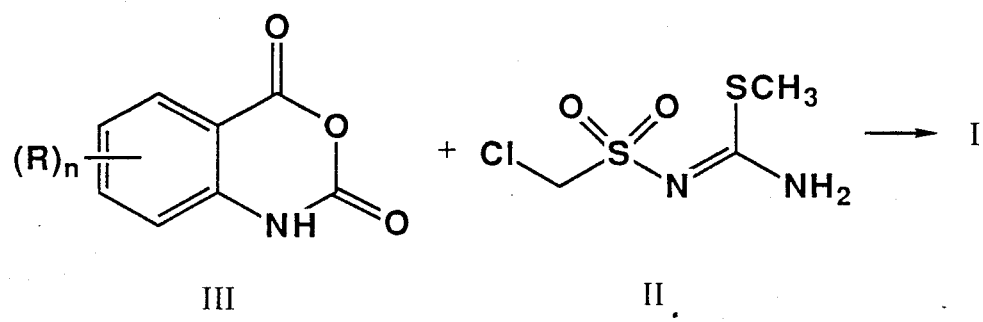
FIG. 2 shows a reaction sequence that can be used to prepare the compounds of the invention.

Referring to the reaction sequence shown as FIG. 2, the reaction of an isatoic anhydride (III) with the known chloromethanesulfonyl isothiourea (II), in an appropriate solvent such as acetonitrile or dioxane and in the presence of a proton acceptor such as sidium hydride, a tertiary amine, or other base, provides the compounds of the invention (I). In both Formulas I and III, each R substituent individually represents halogen, hydroxyl, lower alkyl (i. e., $C_1$ to $C_6$ alkyl), $OR^1$ (wherein $R^1$ represents lower alkyl, optionally substituted by $R^2R^3N$—CO—, wherein $R^2$ and $R^3$ individually represent lower alkyl or cycloalkyl), nitro, amino (optionally substituted by $R^1$, wherein $R^1$ is as described above), or $R^1S(O)_x$ (wherein $R^1$ is as described above, and x=0,1, or 2), and represents a number having a value of from 0 to 4, and n preferably from 0 to 2.

The thiadiazole compounds of the invention can be produced from an isatoic anhydride of Formula III via the general reaction shown in FIG. 2, so long as the group or groups represented by the R variable in Formulas I and III are not chemically reactive under the conditions of the reaction. Examples 2–8, below, illustrate representative reaction conditions that can be used to produce the thiadiazole compounds of the invention from the corresponding isatoic anhydride.

Many of the isatoic anhydrides that are used as starting reactants in the synthesis of the compounds of the invention are known compounds. Isatoic anhydrides can be produced by the procedures described by G. Coppola et al. in J. Het. Chem., 22, 193 (1985) and G. Coppola, Synthesis, 505 (1980).

The isatoic anhydride is reacted with (II) in approximately equimolar proportions, in a suitable reaction medium in the presence of an acid acceptor such as a tertiary amine or alkali metal hydride. The reaction is preferably carried out under an inert atmosphere such as nitrogen or argon. The reaction is carried out at a temperature and for a period of time sufficient to produce the desired compound. Usually, it is most convenient to carry out the reaction under atmospheric reflux conditions for a period of time within the range of from about 1 to about 24 hours. The reaction temperature will usually be from about 50° C. to about 120° C. Upon the completion of the reaction, the reaction mixture is cooled and the desired product is recovered by standard procedures. For example, the cooled reaction mixture may be poured into an aqueous acid such as citric, acetic, or hydrochloric acid, which will precipitate the desired product compound. The compound may then be recovered by filtration and may be purified by recrystallization from a suitable solvent. The examples, below, illustrate representative reaction conditions that have been found to be effective in producing the compounds of the invention.

The invention also provides an improved process for the synthesis of (II) in which S-methylisothiourea (as the salt of an inorganic acid) is sulfonylated by chloromethanesulfonyl chloride in a two-phase system in the presence of an inorganic base, water, and an organic solvent such as methylene chloride that is substantially immiscible with water.

The compounds of this invention have shown activity as inhibitors of cyclic nucleotide phosphodiesterase, and thus are potentially useful as cardiotonic agents. Inhibitors of cyclic nucleotide phosphodiesterase frequently act to inhibit platelet aggregation. Therefore, the compounds of this invention may also have utility as antithrombotic agents.

EXAMPLE 1

Preparation of
S-methyl-N-(chloromethanesulfonyl)isothiourea (II).

Water (250 ml) is added with stirring to a slurry of S-methylisothiourea sulfate (77.3 g, 0.556 mol) and sodium carbonate (273 g, 2.58 mol) in methylene chloride (1100 ml). Chloromethanesulfonyl chloride (85% pure, 94.8 g, 0.542 mol) is then added slowly with stirring at such a rate as to maintain gentle reflux of the solvent. The mixture is then stirred at room temperature for 16 hr, and the organic solution is decanted from the inorganic residue. The residue is washed with additional methylene chloride (500 ml), and the combined organic solutions are dried with magnesium sulfate, filtered, and concentrated to leave crude II as a yellow oil (99.5 g, 90%). This crude material is adequate for preparing the thiadiazole compounds of the invention (e.g., see Example 4, below). Purification by chromatography on silica gel (2.5% ethyl ether in methylene chloride as eluant) provides the title compound as a colorless solid, mp 60°–62° C. (72 g, 65%).

In the preparation of II, the preferred solvent is methylene chloride, as is illustrated in the foregoing Example. It may be replaced by other organic solvents in which water is less than about 2% soluble, such as chloroform, diethyl ether, benzene, or toluene. Solvents in which water is more soluble, such as ethyl acetate, are less satisfactory. The preferred inorganic base for use in this process is sodium carbonate. Satisfactory substitutes are, for instance, sodium bicarbonate, potassium carbonate, and potassium bicarbonate. The reaction temperature is most conveniently the boiling point of methylene chloride, but may be varied between about 0° C. to about 60° C. The reaction is essentially complete within one hour, and longer reaction times do not affect the yield. The proportion of added water may be varied. In the foregoing Example, 200 to 400 ml could be used. The proportion of organic solvent has been chosen for convenience, and it is anticipated that the volume can be reduced.

EXAMPLE 2

Preparation of Thiadiazoles (I)

7-Nitro-1H-1,2,4-thiadiazolo[3,4-b]quinazolin-5-one-2,2-dioxide.

To a stirred solution of 5-nitroisatoic anhydride (1.04 g, 5.0 mmol) and S-methyl-N-(chloromethanesulfonyl)isothiourea (1.04 g, 5.0 mmol) in acetonitrile (10 ml) under nitrogen is added 4-(N,N-dimethylamino)-pyridine (0.61 g, 5.0 mmol). The solution is refluxed for 16 hr, cooled, and poured into 10% aqueous citric acid. The resulting solid is collected by filtration and recrystallized twice from isopropanol/DMF, then from DMSO, to provide the title compound as a light yellow solid, mp >300° C. (225 mg, 16%).

EXAMPLE 3

7,8-Dimethoxy-1H-1,2,4-thiadiazolo[3,4-b]quinazolin-5-one-2,2-dioxide.

To a stirred slurry of 4,5-dimethoxyisatoic anhydride (4.46 g, 20 mmol) and S-methyl-N-(chloromethanesulfonyl)isothiourea (4.06 g, 20 mmol) in dioxane (30 ml) is added 1,5-diazabicyclo[4.3.0]non-5-ene (2.5 ml). The mixture is refluxed for 4 hr under nitrogen, then cooled and poured into 0.3N aqueous hydrochloric acid. The precipitate is collected by filtration and recrystallized from DMSO to provide the title compound as a light yellow solid, mp >300° C. (445 mg, 7.5%).

EXAMPLE 4

6,7-Dimethoxy-1H-1,2,4-thiadiazolo[3,4-b]quinazolin-5-one-2,2-dioxide.

To a stirred solution of 5,6-dimethoxyisatoic anhydride (8.93 g, 40 mmol) and S-methyl-N-(chloromethanesulfonyl)isothiourea (90% pure, 9.73 g, 44 mmol) in N-methyl-2-pyrrolidinone (50 ml) under nitrogen is added sodium hydride (1.65 g of 60% dispersion in oil, 41 mmol). After 15 min at room temperature, the mixture is stirred at 80° C. for 18 hr, then cooled and poured into 0.5N aqueous hydrochloric acid (150 ml). The precipitate is collected by filtration, and washed with water, then with ether. Recrystallization from DMF containing 5% water provides the title compound as a tan solid, mp >300° C. (2.55 g, 21%).

EXAMPLE 5

7,8-Dichloro-1H-1,2,4-thiadiazolo[3,4-b]quinazolin-5-one-2,2-dioxide.

To a stirred slurry of 4,5-dichloroisatoic anhydride (11.54 g, 50 mmol) in N-methyl-2-pyrrolidinone (50 ml) under nitrogen is added sodium hydride (2.05 g of 60% oil dispersion, 52 mmol). The mixture is stirred for 30 min at room temperature, and to the resulting solution is added S-methyl-N-(chloromethanesulfonyl)-isothiourea (11.0 g, 55 mmol). The mixture is stirred under nitrogen at 80° C. for 18 hr, then worked up as in Example 4 above. Recrystallization from DMF provides the title compound as a white solid, mp >300° C. (4.69 g, 31%).

EXAMPLE 6

7-Chloro-1H-1,2,4-thiadiazolo[3,4-b]quinazolin-5-one-2,2-dioxide.

To a stirred slurry of 5-chloroisatoic anhydride (5.93 g, 30 mmol) and S-methyl-N-(chloromethanesulfonyl)isothiourea (6.08 g, 30 mmol) in dioxane (50 ml) is added 4-(N,N-dimethylamino)pyridine (3.67 g, 30 mmol). The mixture is refluxed under nitrogen for 24 hr, then worked up as in Example 4 above. Recrystallization from DMF provides the title compound as a white solid, mp >300° C. (1.24 g, 15%).

EXAMPLE 7

8-Chloro-1H-1,2,4-thiadiazolo[3,4-b]quinazolin-5-one-2,2-dioxide.

To a stirred slurry of 4-chloroisatoic anhydride (4.95 g, 25 mmol) and S-methyl-N-(chloromethanesulfonyl)isothiourea (5.07 g, 25 mmol) in acetonitrile (25 ml) under nitrogen is added 4-(N,N-dimethylamino)pyridine (3.97 g, 33 mmol). The mixture is refluxed under nitrogen for 24 hr, concentrated, then worked up as in Example 4 above. The resulting gummy solid is triturated with hot ethanol, then recrystallized from DMF to provide the title compound as a white solid, mp >300° C. (1.65 g, 24%)

EXAMPLE 8

1H-1,2,4-Thiadiazolo[3,4-b]quinazolin-5-one-2,2-dioxide.

To a stirred slurry of isatoic anhydride (3.10 g, 19 mmol) and S-methyl-N-(chloromethanesulfonyl)isothiourea (3.85 g, 19 mmol) in acetonitrile (30 ml) under nitrogen is added 4-(N,N-dimethylamino)pyridine (2.32 g, 19 mmol). The mixture is refluxed under nitrogen for 16 hr, concentrated, then worked up as in Example 4 above. Recrystallization from DMF provided the title compound as a white solid, mp >300° C. (1.32 g, 29%).

EXAMPLE 9

7-(N-Cyclohexyl-N-methyl-4-amino-4-oxobutyloxy)-1H-1,2,4-thiadiazolo[3,4-b]quinazolin-5-one-2,2-dioxide.

To a stirred solution of 5-hydroxy-2-nitrobenzaldehyde (29.8 g, 0.178 mol) and ethyl 4-bromobutyrate (26.8 ml, 0.187 mol) in DMF under nitrogen is added potassium carbonate (25.1 g, 0.182 mol). The mixture is heated to 90° C. and stirred at this temperature for 2 hr, then poured into 1500 ml ice water. The mixture is extracted with ethyl ether (5×300 ml), and the ether extracts are washed with water and dried over magnesium sulfate, filtered, and concentrated to provide 45.7 g (91%) 5-(4-ethoxy-4-oxobutoxy)-2-nitrobenzaldehyde as a yellow oil. This material is dissolved in ethanol (350 ml), and potassium hydroxide (11.3 g) in water (180 ml) is added. The mixture is stirred at room temperature for 3 hr then partially evaporated to remove the ethanol. The aqueous solution is washed with ethyl ether and then acidified with 6N HCl (50 ml). The mixture is then extracted with chloroform and the organic solution dried with magnesium sulfate, filtered, and concentrated to a volume of 100 ml. Addition of hexane precipitates a yellow solid, which is collected by filtration to provide 5-(3-carboxypropyloxy)-2-nitrobenzaldehyde, mp 112°–114° C. (37.2 g, 91%).

This material is suspended in 200 ml benzene, and oxalyl chloride (32 ml, 0.366 mol) is added. The resulting mixture is stirred under nitrogen and heated to reflux for 5 min, then cooled to room temperature and stirred for 1 hr. The resulting solution is evaporated to leave the acid chloride as a brown oil. This is dissolved in tetrahydrofuran (50 ml), and added dropwise to a stirred solution of N-methyl cyclohexylamine (50 ml) in tetrahydrofuran (100 ml) kept at 5°–10° C. After 2 hr, the mixture is concentrated, and the residue dissolved in ethyl acetate and washed three times with 1N HCl, once with water, and once with 1N NaOH. The organic solution is then dried with magnesium sulfate, filtered, and concentrated to provide a brown oil. Trituration with diethyl ether (300 ml) provides 43.5 g (85%) 5-(N-cyclohexyl-N-methyl-4-amino-4-oxobutyloxy)-2-nitrobenzaldehyde as a tan solid, mp 98°–100° C.

This material (17.4 g, 0.05 mol) is added to a slurry of silver(I) oxide (5.91 g, 0.026 mol) in 53 ml 1N NaOH, and the mixture stirred for 6 hr at 60° C., then cooled and filtered through Celite. The filtrate is washed with ethyl ether, then brought to pH 1.0 with conc. HCl. The mixture is then extracted with methylene chloride (4×200 ml), and the organic extracts are dried with magnesium sulfate, filtered, and concentrated to provide a brown gum. Chromatography on silica gel with 45:45:9:1 methylene chloride:dichloroethane:isopropanol:acetic acid provides 5-(N-cyclohexyl-N-methyl-4-amino-4-oxobutyloxy)-2-nitrobenzoic acid (11.5 g, 63%) as a non-crystalline foam after solvent removal. Hydrogenation of the above acid (10.7 g, 29.4 mmol) in ethanol (100 ml) over 10% Pd/Carbon under 50 psi hydrogen for 2 hr provides, after filtration and solvent removal, 9.75 g (99%) 5-(N-cyclohexyl-N-methyl-4-amino-4-oxobutyloxy)-2-aminobenzoic acid as a yellow foam. This material is refluxed with ethyl chloroformate (11 ml) under nitrogen for 18 hr. The solution is cooled, and acetyl chloride (40 ml) is added dropwise with stirring. This mixture is refluxed for 6 hr, then cooled. The resulting precipitate is collected by filtration, and washed with carbon tetrachloride, providing 5-(N-cyclohexyl-N-methyl-4-amino-4-oxobutyloxy)isatoic anhydride (4.73 g, 45%) as a grey solid, mp 222°–224° C.

The above isatoic anhydride (3.60 g, 10 mmol) is converted by the method of Example 4 (above) to the title compound, obtained after chromatography on silica gel (4% isopropanol in methylene chloride as eluant) as a colorless solid, mp >330° C. (0.69 g, 16%).

BIOLOGICAL ACTIVITY

The compound of Example 9 has an $IC_{50}$ of 13 $\mu$M versus cyclic nucleotide phosphodiesterase fraction III. When this compound was administered to a dog intravenously at 1.9 mg/kg, cardiac force increased 37%.

Biological Assay Tests

Procedure I

Cyclic Nucleotide Phosphodiesterase Assay

Literature Reference:

Thompson, W. J., Terasaki, W. L., Epstein, P. M. and Strada, S. J. Assay of Cyclic Nucleotide Phosphodiesterase and Resolution of Multiple Molecular Forms of the Enzyme. In *Advances in Cyclic Nucleotide Research*, ed. by G. Brooker, P. Greengard, and G. A. Robioson Vol. 10 (1979), pp. 69–92.

Test Object:

Heart, Lung, and Other Tissues

Procedures:

This assay measures the ability of compounds to inhibit cyclic nucleotide phosphodiesterase. This enzyme converts either cyclic AMP or cyclic GMP to the non-cyclized AMP or GMP, respectively. Compounds are tested at various concentrations in the presence of cyclic AMP (0.10–1.0 $\mu$M containing 0.2 $\mu$Ci $^3$H-cyclic AMP), enzyme, and 0.05M Tris-Cl buffer (pH 7.4, containing 5 mM $MgCl_2$). After a specified time, the reaction is stopped by heating to 100° C. for 1 min. After cooling, 0.10 ml of a solution containing snake venom (1 mg/ml) is added and the reaction is allowed to proceed for 30 min. Termination of this reaction is accomplished by the addition of 1.0 ml of 33% Dowex slurry to separate the product from unconverted substrate. An aliquot is removed from the supernatant and quantitated by liquid scintillation spectrometry.

Analysis:

Data is presented as the $IC_{50}$ which is the concentration ($\mu$M) of compound required to inhibit 50% of the cyclic nucleotide phosphodiesterase activity.

Procedure II

INHIBITION OF CALCIUM DEPENDENT SMOOTH MUSCLE CONTRACTION

Literature References:

Farley, J. M. and Miles, P. R. The Sources of Calcium for Acetylcholine-Induced Contractions of Dog Tracheal Smooth Muscle. J. Pharmacol. Exp. Ther. 207: 340–346,1 1978.

Test Object:

Canines, guinea pigs and rabbits

Procedure:

Trachea from dogs killed by excess KCl injection are stored overnight at 4° C. in oxygenated Krebs-Henseleit buffer. Tracheal rings, one cartilage segment wide (5-10 mm), are cut starting from the bronchial end. After cutting the cartilage, the trachealis muscle tissue is suspended in oxygenated Krebs-Henseleit buffer at 37° C. in a 25 ml tissue bath. After a 60 minutes equilibration period, the tissues are challenged with 10 μM carbachol. After 5 minutes the tissues are rinsed and allowed to rest 50 minutes. The tissues are then challenged with 50 mM KCl and, after 30 minutes, the contractions are quantitated. The tissues are then rinsed and reequilibrated for 50 minutes. Test compounds are then added for 10 minutes, and the tissue is rechallenged with 50 mM KCl. After 30 minutes, the contraction is recorded and used to determine the % inhibition of control.

Analysis:

The percent inhibition of smooth muscle contraction is calculated from response data before and after drug treatment.

$$\% \text{ inhibition} = 100 - 100(x), \text{ wherein:}$$

$$x = \frac{\text{(peak response after drug treatment)}}{\text{(peak response before drug treatment)}}$$

Procedure III

Acute In Vivo Cardiotonic Evaluation

Literature Reference:

Cardiotonic Activity of Amrinone-Win 40680. Alousi, A. A., Farah, A. I., Lester, G. Y. and Opalka, C. J. Circ. Res. 45:666, 1979.

Test Object:

Dog

Procedure:

Adult mongrel dogs are anesthetized with sodium pentobarbital and artifically respired. Arterial pressure is recorded via a femoral artery and the pressure pulse is used to trigger a cardiotachometer for heart rate. Left ventricular pressure is measured with a Millar catheter and dP/dt is derived. Cardiac output is determined by measuring ascending aortic blood flow with an electromagnetic flow probe and myocardial contractile force is measured with a Walton Brodie strain gauge sutured to the right ventricle. Lead II EKG is also recorded.

A standard dose of dopamine or dobutamine is administered to assess myocardial responsiveness.

Test compounds are administered by i.v. infusion or bolus administration and the effects on cardiovascular parameters are determined.

Analysis:

Dose related effects of the test compound on blood pressure, heart rate, dP/dt max. (dp/dt represents the rate at which blood pressure rises), cardiac force, and cardiac output are compared to pretreatment control values, expressed as a % change and rated for activity. Statistical evaluations are made using the appropriate parametric test against a vehicle control.

The compounds of Examples 2-9 were subjected to various combinations of the foregoing biological assay procedures. The results are as follows:

| Example No. | Procedure I $IC_{50}$ (μM) | Procedure II % inhibition (dose μM) | Procedure III % Change CF (dose mpk) |
|---|---|---|---|
| 2 | — | 9% (10) | — |
| 3 | 35 | 13% (2) | 8% (1.9) |
| 4 | — | 43% (2) | 22% (1.9) |
| 5 | — | 11% (2) | — |
| 6 | 70 | 18% (10) | — |
| 7 | 150 | 31% (10) | — |
| 8 | 150 | 20% (10) | — |
| 9 | 13 | — | 37% (1.9) |

In interpreting the results tabulated above, Procedure I gives the concentration of drug that inhibits the enzyme by 50%, Procedure II indicates potential utility as a broncho-dilator, as revealed by inhibition of muscle contractility at the given dose, and Procedure III indicates enzyme inhibition in the tissue, as revealed by an increase in cardiac force (CF).

What is claimed is:

1. A 1H-1,2,4-thiadiazolo[3,4-b]quinazoline-5-one-2,2-dioxide of the Formula:

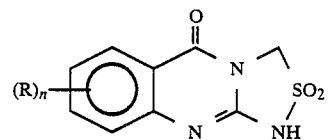

wherein each R individually represents halogen, hydroxyl, lower alkyl, $OR^1$, wherein $R^1$ represents lower alkyl which may be substituted by $R^2R^3N-CO-$ wherein $R^2$ and $R^3$ individually represent lower alkyl or cycloalkyl, nitro, amino which may be substituted by $R^1$ wherein $R^1$ is as described above, or $R^1S(O)_x$ wherein $R^1$ is as described above and wherein x represents a number having a value of from 0 to 2, and wherein n represents a number having a value of from 0 to 4.

2. The compound of claim 1 which is 7-nitro-1H-1,2,4-thiadiazolo-[3,4-b]quinazolin-5-one-2,2-dioxide.

3. The compound of claim 1 which is 7,8-dimethoxy-1H-1,2,4-thiadiazolo[3,4-b]quinazolin-5-one-2,2-dioxide.

4. The compound of claim 1 which is 6,7-dimethoxy-1H-1,2,4-thiadiazolo[3,4-b]quinazolin-5-one-2,2-dioxide.

5. The compound of claim 1 which is 7,8-dichloro-1H-1,2,4-thiadiazolo[3,4-b]quinazolin-5-one-2,2-dioxide.

6. The compound of claim 1 which is 7-chloro-1H-1,2,4-thiadiazolo[3,4-b]quinazolin-5-one-2,2-dioxide.

7. The compound of claim 1 which is 8-chloro-1H-1,2,4-thiadiazolo[3,4-b]quinazolin-5-one-2,2-dioxide.

8. The compound of claim 1 which is 1H-1,2,4-thiadiazolo[3,4-b]-quinazolin-5-one-2,2-dioxide.

9. The compound of claim 1 which is 7-(N-cyclohexyl-N-methyl-4-amino-4-oxobutyloxy)-1H-1,2,4-thiadiazolo[3,4-b]-quinazolin-5-one-2,2-dioxide.

10. A method for increasing the cardiac output of a mammal which comprises administering to a mammal an effective dose of a compound of claim 1.

11. The method of claim 10 wherein the compound is the compound of claim 9.

* * * * *